United States Patent [19]
Pelle et al.

[11] Patent Number: 6,136,301
[45] Date of Patent: Oct. 24, 2000

[54] LIPID MIX FOR LIP PRODUCT

[75] Inventors: Edward Pelle, Valley Stream; Kenneth D. Marenus; Christina G. Fthenakis, both of Dix Hills; H. Peter Norden, Smithtown, all of N.Y.

[73] Assignee: E-L Management Corp., New York, N.Y.

[21] Appl. No.: 08/865,821

[22] Filed: May 30, 1997

[51] Int. Cl.[7] .......................... A61K 7/021; A61K 7/025; A61K 7/06; A61K 7/00

[52] U.S. Cl. .............................. 424/63; 424/64; 424/70.1; 424/401

[58] Field of Search ................ 424/64, 63, 70.1, 424/401

[56] References Cited

U.S. PATENT DOCUMENTS

| | | | |
|---|---|---|---|
| 3,821,372 | 6/1974 | Vanlerberghe et al. | 424/170 |
| 3,928,224 | 12/1975 | Vanlergerghe et al. | 252/172 |
| 4,087,466 | 5/1978 | Vanlerberghe et al. | 260/615 |
| 4,610,868 | 9/1986 | Fountain et al. | 424/1.1 |
| 5,053,229 | 10/1991 | Hattori | 424/572 |
| 5,618,523 | 4/1997 | Zysman | 424/70.1 |

FOREIGN PATENT DOCUMENTS

| | | |
|---|---|---|
| 1477048 | 4/1967 | France . |
| 1539625 | 1/1979 | United Kingdom . |
| 83/01571 | 5/1983 | WIPO . |
| 94/00127 | 6/1994 | WIPO . |

OTHER PUBLICATIONS

Peter M. Elias, M.D., Epidermal Lipids, Barrier Function, and Desquamation,–J. Invest. Dermatol. 80 (6) Supp.: 44, 1983.

Scanu, A. M., Spector, A. A. (Eds.), "Biochemistry and Biology of Plasma Lipoproteins", pp. 223–245 (Marcel Dekker, Inc. 1985).

Elias, P. M. (Ed.), "Advances in Lipid Research, vol. 24, Skin Lipids", pp. 1–56 (Academic Press, Inc., 1991).

Strauss, J. F., Menon, K. M. J., "Lipoprotein and Cholesterol Metabolism in Steroidogenic Tissues", pp. 1–32 (George F. Stickley Company, 1985).

*Primary Examiner*—John Kight
*Assistant Examiner*—D. Faulkner
*Attorney, Agent, or Firm*—Dorene M. Price, Esq.; Karen A. Lowney, Esq.

[57] ABSTRACT

The invention relates to lipid mixture compositions comprising one or more cholesteryl esters in an amount of at least about 25% by weight of the composition, and less than about 5% by weight of sphingolipid, as well as cosmetic and pharmaceutical formulations for topical application to the lips containing the lipid mixture.

28 Claims, No Drawings

LIPID MIX FOR LIP PRODUCT

FIELD OF THE INVENTION

The present invention relates to cosmetic and therapeutic compositions for the lips. More specifically, the invention relates to lip compositions comprising a unique blend of lipids for lip treatment.

BACKGROUND OF THE INVENTION

Skin is typically characterized as consisting of three distinct layers, namely the stratum corneum, the epidermis and the dermis. The stratum corneum, the outermost layer, is made up of keratinized cells, surrounded by intercellular space filled with lipids. The stratum corneum provides a substantial physical barrier to penetration of most substances to the lower layers of the skin. In addition to preventing transport of substances to the other skin layers, however, this barrier also aids in prevention of water loss from the skin. Both functions are primarily attributable to the presence of the lipids in the stratum corneum.

There are two sources of the skin surface lipids making up this important barrier: sebaceous glands and the epidermis. The lipids are a diverse group of compounds, comprising triglycerides, diglycerides, ceramides, free fatty acids, wax esters, cholesterol and cholesterol esters, and squalene. The quantity and composition of the skin surface lipids differ from place to place on the body, and may to some extent be related to the number of sebaceous glands in a given area of the skin. The condition of the skin surface lipids may also be affected by an essential fatty acid deficiency. Additionally, the lipid barrier is easily diminished by exposure to harsh detergents or soaps and other environmental factors. It is apparent, then, that the quality of the skin lipid barrier can vary widely, depending on a number of different factors, and therefore, may not always be adequate to perform its protective function optimally.

As an attempt to compensate for what may be a less than adequate lipid barrier, cosmetic compositions frequently incorporate components which compensate for water loss. Examples of such materials are hygroscopic humectants, e.g., urea or propylene glycol; or emollients, e.g., oleyl alcohol or caprylic/capric triglycerides. Certain cosmetic components may be occlusive skin conditioners, which are used to provide an "artificial" barrier; such compounds are frequently hydrophobic materials which remain on the skin surface, and include various hydrogenated oils, waxes and butters. Although many of these products provide an effective means of stemming water loss from the skin, they do not generally constitute a natural-occurring component of the stratum corneum, potentially giving rise to an unnatural, greasy feel to the skin. In addition, various pharmaceutical or cosmetic active agents are also frequently used to treat the symptoms of dry skin-associated conditions; however, in many cases, particularly with pharmaceutical agents, the treatments themselves may cause undesirable side effects in the individual being treated, while ultimately resulting in no actual reconstitution or repair of the lipid barrier.

In recent years, considerable study has been devoted to efforts to determine the normal lipid composition of the skin. In order to repair or maintain the integrity of the barrier, it is important to know what the normal, fully functional state of the barrier should be. For example, Elias (J. Invest. Dermatol. 80(6)Supp.:44, 1983) discloses a naturally-occurring lipid composition, apparently from human abdomen epidermis, containing relatively large quantities of sphingolipids, free sterols, cholesterol sulfate, and free fatty acids. In particular, the fatty acids, particularly the fatty acid portions of the sphingolipid components, are said to be enriched in long-chain, fully saturated acyl groups. WO 94/00127 further discloses synthetic lipid compositions comprising as its main components cholesterol, ceramides, and fatty acids. Apparently based at least in part on the reported composition of the natural epidermal lipid barrier, these compositions are said to be useful in moisturizing and lipid barrier fortification and repair.

However, to date, there have been no studies conducted on lip lipid compositions. The lips provide a unique problem, in that, unlike other areas of the body, they are virtually always exposed to seasonal environmental hazards, such as wind, cold and sun, and are therefore susceptible to frequent chapping, cracking and dryness. In addition, many lip cosmetics, such as traditional lipsticks, may contribute to the dryness. Although there are lip products which are aimed at treating or preventing this problem, these are primarily of the "artificial barrier" type, and are not capable of repairing or reconstituting the natural lipid barrier. Thus, there continues to be a need for a treatment regimen and composition which specifically addresses the singular difficulties associated with maintaining and treating the lip area. The present invention now fills this need.

SUMMARY OF THE INVENTION

The present invention provides lipid compositions, useful in cosmetic and therapeutic lip products, which mimic the unique lipid composition of the lips. In particular, the lipid compositions comprise, relative to reports of the lipid compositions of the epidermis in other regions of the body, a lipid component containing high levels of cholesteryl esters, and little or no sphingolipid. Specifically, the amount of cholesteryl ester is at least about 25%, and sphingolipids at an amount of less than 5%. The lipid composition also comprises fatty acids and triglycerides, in amounts of at least about 10%. The lipid compositions of the invention, in combination with an appropriate vehicle, can be incorporated into cosmetic products, such as lipsticks, as well as in therapeutic products, such as lip balms.

The compositions of the invention are useful in repairing a damaged lip lipid barrier or maintaining a healthy lip lipid barrier. Also, the invention relates to a method of treating or preventing damage to the lips, wherein the damage is associated with a reduction or loss of lipid barrier function.

DETAILED DESCRIPTION OF THE INVENTION

It has been unexpectedly discovered that the lipid composition of the lips differs from that disclosed for the stratum corneum found on other areas of the body. An analysis of human lip lipids reveals that, unlike other epidermal regions, the lip epidermis contains a relatively high level of cholesteryl esters and only trace amounts of sphingolipids. As an example of typical epidermis, Elias (supra) discloses that stratum corneum from the abdomen contains only about 5% sterol/wax esters, and about 18% sphingolipids, the primary sphingolipids being ceramides. In contrast, it has been surprisingly found that cholesteryl esters represent a very large component, i.e., at least about 25%, of the lip lipid composition. Concurrently, it was also found that ceramides, or sphingolipids generally, are present in only trace amounts. The lip lipid composition also comprises significant quantities of triglycerides and fatty acids, but in amounts which are not drastically different from those found in regular epidermis. However, these data make it apparent that lipid compositions designed to mimic the average epidermal lipid barrier will not serve the same function when applied to lips.

The knowledge of the composition of the lip lipid barrier makes it possible to design a synthetic lipid composition which can be used to effect lip barrier repair or maintenance, a function not heretofore possible. The term "synthetic" as used herein is used solely to distinguish the composition of the invention from the naturally-occurring collection of lipids found in situ on the lips. The lipid composition comprises from about 25 to about 60%, by weight of the total lipid composition, of one or more cholesteryl esters. Preferably, the cholesteryl ester component constitutes at least 30%, and more preferably, at least 40%, by weight of the total lipid composition. The cholesteryl ester used may be any cholesteryl ester or a mixture of esters; however, analysis of the lip lipid composition indicates that the natural cholesteryl ester component comprises mainly short chain esters. In a preferred embodiment, therefore, the ester portion of the cholesteryl ester is one or more $C_2$–$C_{16}$ esters, for example, cholesteryl acetate, cholesteryl butyrate, cholesteryl caprylate, cholesteryl octanoate, cholesteryl decanoate, cholesteryl palmitate or cholesteryl stearate. Particularly preferred are $C_2$–$C_8$ cholesteryl esters.

The lipid composition also comprises a glyceride component. By "glyceride" in the present context is meant any compound which is an esterification product of one or more fatty acids and glycerol. The glyceride component may contain one or more mono-, di- or triglycerides, or a mixture thereof. This component is present in an amount of from about 5% to about 40% by weight of the total lipid composition, more preferably about 10–35%. The higher levels of the glyceride are desirable so as to render the composition more compatible with a typically highly hydrophobic wax lipstick base, and also to enhance moisturization. Preferably, the glyceride component comprises primarily di- and triglycerides, and in a particularly preferred embodiment, the glyceride ester side chains are saturated, so as to hinder potential oxidation. Examples of useful glycerides are glyceryl palmitate, glyceryl caprylate, glyceryl myristate, and glyceryl stearate.

The lipid composition also contains a free fatty acid component. This component may comprise one or more free fatty acids in an amount of from about 5% to about 40% by weight of the total lipid composition, more preferably from about 10 to about 35%. Any fatty acid can be used; however, it is preferred, for practical purposes, to use fatty acids which are not highly unsaturated, i.e., having two or more unsaturated bonds, so as to avoid the potential for oxidation. Examples of useful fatty acids are butyric acid, caproic acid, octanoic acid, decanoic acid, dodecanoic acid, tetradecanoic acid, palmitic acid, stearic acid, and oleic acid. Particularly preferred are fatty acids with a $C_{14-18}$ chain length. In one preferred embodiment, a combination of one saturated and one monounsaturated fatty acid is employed. Preferred fatty acids are oleic and palmitic acids, as these are the primary naturally occurring free fatty acids in the stratum corneum.

The lipid composition may contain additional optional components as well. Cholesterol is a significant component of the naturally occurring lip lipid composition, and may be added to the mixture in an amount of up to about 25%. In addition, small amounts, preferably no more than about 3–10%, of alkene and alkane lipid components may also be included.

A particularly distinctive aspect of the preferred lipid compositions of the invention is the low level of sphingolipids, particularly ceramides. Unlike the previously known compositions, the present compositions comprise less than 5%, preferably less than 1%, more preferably less than 0.5%, of a sphingolipid.

In one embodiment of the invention, the lipid mixture comprises cholesteryl esters, glycerides and fatty acids in a weight ratio of about 3:1:1 to about 1:1:1, respectively.

The lipid compositions of the present invention, for ease of application to the lip area, are combined with a cosmetically or pharmaceutically acceptable carrier or base. The base may be of any type which is appropriate for use on the lips and around mucous membranes. The vehicle may take the form of creams, lotions, gels, solutions, sprays, and the like. A particularly preferred form of base, however, will be a waxy base, more typically an anhydrous waxy base, as is usual for most products intended for application to the lips. Methods for formulating such wax based products are well known in the art. Briefly, a typical waxy base contains one or more waxes, one or more oils, and one or more surfactants to aid in dispersing the components. "Waxes" as used herein intended to comprise not only waxes in the traditional sense, i.e., those plant, animal or mineral waxes containing primarily esters of higher fatty acids and alcohols, free higher acids and alcohols, and saturated hydrocarbons, but also synthetic resinous products having a wax-like, i.e., hard, brittle, relatively non-greasy, texture, such as silicone waxes. Examples of suitable waxes for use in the wax base include, but are not limited to, carnauba wax, candelilla wax, beeswax, synthetic wax, shellac wax, spermaceti, lanolin wax, ozokerite, bran wax, ceresin wax, bayberry wax, paraffin, rice wax and jojoba wax. "Oils" as used herein encompass not only naturally occurring plant, animal and mineral oils, but also oil-like emollients, such as fatty esters, fatty alcohols, and silicone oils. The surfactant may be any that is routinely used in this type of product. Examples of components useful in formulating cosmetic bases are found, for example, in the International Cosmetic Ingredient Handbook, CTFA, 1996, contents of which are incorporated herein by reference. The lipid component is added to the base in an amount of from about 0.1 to about 60% total lipid, preferably from about 1–20%, more preferably from about 1–10%. It will be apparent that the lipids can be added to the base in the form of a premix, with all the components already combined, or the lipid components can be added to the base individually. Therefore, as used in the present specification and claims, the term "mixture" as applied to the lipid combinations as incorporated in cosmetic or pharmaceutical formulations, will be understood to encompass both a premade mixture, as well as the mixture of the lipids which have been added individually to the formulation.

The formulations of the present invention can be used for both cosmetic and pharmaceutical applications. For example, the formulation may take the form of a cosmetic, such as a lipstick or lip gloss, wherein the lipid mixture potentially has both a therapeutic and maintenance effect. In addition, the formulation may be completely therapeutic, for example, intended to be used in application to lips which are in need of lipid barrier repair or fortification due to the damaging effects of diseases, chronic or acute conditions, or environmental insult. Given the various uses of the lipid mix-containing formulations, therefore, it will be understood that the formulations also can comprise other components which are chosen depending on the carrier and/or the intended use of the formulation. Examples of additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); emollients (such as petrolatum); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

In certain embodiments, it may be particularly desirable to combine the therapeutic effect of the lipid mixture with other active components intended for therapeutic treatment of the lip area. Examples of such actives include antiinflammatories, antihistamines, antiirritants, antibiotics, antivirals, antifungals, and antipruritics. Examples of conditions which can benefit from application of such combinations include, but are not limited to, ulcers, blisters, herpes virus infections, severe chapping, or burns. Methods and/or regimens for application of the lip products of the invention are in accordance with the normal usage of products of similar type, i.e., lipsticks, lip balms, ointments, etc.. Additional uses of the formulations of the invention will be readily apparent to those skilled in the art.

The invention is further illustrated by reference to the following non-limiting examples.

EXAMPLES

Example 1

This example describes analysis of the lipid content of human facial lips:

A 9 mm diameter polypropylene cup is held firmly on the lip. This is followed by washing of the lip with 0.5 ml of solvent, either ethanol or hexane. The washing step is repeated on another area of lip and the two washes pooled, taken to dryness and resuspended in 50 ml of chloroform.

Varying amounts of the resuspended material are spotted onto TLC plates and chromatographed according to Melnick et al.(J. Invest. Dermatol. 92:231, 1989). Lipids are then visualized by acid treatment and charring. They are identified by their mobility on the plate to those of known standards with a densitometer. Similarly, their concentrations are determined by their absorption as compared to the same standards.

The components found in an ethanol extraction are shown below. From this plate, cholesterol, fatty acids, triglycerides, cholesteryl esters, and squalene can be identified. Possibly, there are traces of cholesterol sulfate and ceramide (not III or IV). In addition, when hexane is used as solvent, alkanes are also observable in trace amounts. The primary components of the extract are as follows:

|  | $\mu g/cm^2$ | Percent |
|---|---|---|
| Cholesterol | 5.00 | 21.3 |
| Fatty acid | 3.51 | 15.0 |
| Cholesteryl ester | 9.82 | 41.9 |
| Triglyceride | 2.12 | 9.0 |
| Squalene | 1.95 | 8.3 |
| Other | 1.05 | 4.4 |

Example 2

A lipid mixture of the invention is prepared as follows:

| Component | Weight % |
|---|---|
| Cholesteryl acetate | 33 |
| Glyceryl dicaprylate | 33 |
| oleic acid | 17 |
| palmitic acid | 17 |

Example 3

A lipstick containing 1% of the lipid mixture is prepared, and used to determine the efficacy of the final product in moisturizing treated lips. Fifteen females, with normal to dry lips, in good health and free of any dermatological disorders, are instructed to use the product at least twice a day except for the days of testing, and to refrain from use of any other lipstick or lip treatment products. Evaluation of lip flakiness is carried out by the D-squame Disc Method, and Image Analysis Evaluation. Specifically, samples are collected on D-Squame discs, two from the top lip and two from the bottom lip. the discs are place on the lips slightly overlapping, pressed firmly and the D-Squame discs are then peeled off. The discs are mounted on clear glass slides and evaluated by image analysis. The imaging parameter analyzed for the evaluation of the lip D-Squame samples is the Integrated Optical Density (IOD), which is defined as the total amount(area)of the D-Squames X the D-Squame density (255-Mn Gray Value). The higher the IOD, the drier the lips; therefore, more squames are deposited on the sample disc. A reduction in IOD represents smoother, less flaky lips.

Compared with baseline values, after 2 weeks of treatment, women using the lipstick experienced a decrease in flakiness averaging about 14%, a statistically significant result, showing that the lipid mixture does improve the condition of the lips.

What is claimed is:

1. A lip lipid mixture comprising one or more cholesteryl esters in an amount of at least about 25% by weight of the composition, at least one di- or triglyceride, or a mixture thereof, at least one fatty acid, and less than about 1% of sphinolipid.

2. The composition of claim 1 in which the glyceride is present in an amount of from about 5% to about 40% by weight of the total composition.

3. The composition of claim 1 in which the fatty acid is present in an amount of from about 5 to about 40% by weight of the total composition.

4. The composition of claim 1 which comprises from about 5 to about 40% di- or triglyceride, or a mixture thereof, and from about 5 to about 40% of at least one fatty acid.

5. The composition of claim 4 in which the di- or triglyceride is selected from the group consisting of glyceryl palmitate, glyceryl caprylate, glyceryl myristate, and glyceryl stearate, or a combination thereof.

6. The composition of claim 4 in which the fatty acid is selected from the group consisting of butyric acid, caproic acid, octanoic acids decanoic acid, dodecanoic acid, tetradecanoic acid, palmitic acid and stearic acid, or a combination thereof.

7. The composition of claim 4 in which the fatty acid comprises at least one saturated fatty acid and at least one monounsaturated fatty acid.

8. The composition of claim 4 which also comprises cholesterol in an amount of up to 25% by weight of the total composition.

9. A cosmetic or pharmaceutical formulation for topical application to the lips, the formulation containing a lipid mixture comprising one or more cholesteryl esters in an amount of at least about 25% by weight of the composition, and less than about 5% by weight of sphingolipid.

10. The formulation of claim 9 in which the mixture also comprises one or more fatty acids.

11. The formulation of claim 9 in which the mixture also comprises one or more glycerides.

12. The formulation of claim 11 in which the glyceride is a di- or triglyceride, or a combination thereof.

13. The formulation of claim 9 in which the mixture also comprises both one or more di- or triglycerides and one or more fatty acids.

14. The formulation of claim 9 in which the mixture also comprises cholesterol.

15. The formulation of claim 9 in which the lipid mixture comprises from about 0.1% to about 60% by weight of the total formulation.

16. The formulation of claim 9 in which the lipid mixture comprises from about 1 to about 20% by weight of the total formulation.

17. The formulation of claim 9 which is a wax-based lip product.

18. The formulation of claim 9 which is a lipstick or a lip balm.

19. A cosmetic or pharmaceutical formulation for topical application to the lips, the formulation containing a lipid mixture, the mixture comprising from about 5 to about 40% of a di- or triglyceride, or a combination thereof, from about 5 to about 40% of at least one fatty acid, up to about 25% cholesterol, and less than 5% sphingolipid.

20. The formulation of claim 19 in which the di- or triglyceride is selected from the group consisting of glyceryl palmitate, glyceryl caprylate, glyceryl myristate, and glyceryl stearate.

21. The formulation of claim 19 in which the fatty acid is selected from the group consisting of butyric acid, caproic acid, octanoic acid, decanoic acid, dodecanoic acid, tetradecanoic acid, palmitic acid and stearic acid, or a combination thereof.

22. The formulation of claim 19 in which the fatty acid comprises at least one saturated fatty acid and at least one monounsaturated fatty acid.

23. The formulation of claim 19 in which the lipid mixture comprises from about 0.1% to about 60% by weight of the total formulation.

24. The formulation of claim 19 in which the lipid mixture comprises from about 1 to about 20% by weight of the total formulation.

25. The formulation of claim 19 which is a wax-based lip product.

26. The formulation of claim 19 which is a lipstick or lip balm.

27. A method for maintaining a healthy lip lipid barrier which comprises applying to the lips an effective amount of a lipid mixture comprising one or more cholesteryl esters in an amount of at least about 25% by weight of the composition, and less than about 5% by weight of sphingolipid.

28. A method of treating or preventing damage to the lips, wherein the damage is associated with a reduction or loss of lipid barrier function, which comprises applying to the lips an effective amount of a lipid mixture comprising one or more cholesteryl esters in an amount of at least about 25% by weight of the composition, and less than about 5% by weight of sphingolipid.

* * * * *